US007700546B2

(12) United States Patent
Mekada et al.

(10) Patent No.: US 7,700,546 B2
(45) Date of Patent: Apr. 20, 2010

(54) THERAPEUTIC AGENT FOR CANCER

(75) Inventors: Eisuke Mekada, Osaka (JP); Shingo Miyamoto, Fukuoka (JP)

(73) Assignee: The Research foundation for Microbial Diseases of Osaka c/o Osaka University, Osaka (JP)

( * ) Notice: Subject to any disclaimer, the term of this patent is extended or adjusted under 35 U.S.C. 154(b) by 0 days.

(21) Appl. No.: 11/917,706

(22) PCT Filed: Jun. 20, 2006

(86) PCT No.: PCT/JP2006/312321
§ 371 (c)(1),
(2), (4) Date: Dec. 14, 2007

(87) PCT Pub. No.: WO2006/137398
PCT Pub. Date: Dec. 28, 2006

(65) Prior Publication Data
US 2009/0105135 A1    Apr. 23, 2009

(30) Foreign Application Priority Data
Jun. 21, 2005  (JP) .............................. 2005-181314
Feb. 3, 2006    (JP) .............................. 2006-027581

(51) Int. Cl.
*A61K 38/00* (2006.01)
(52) U.S. Cl. ......................................................... 514/2
(58) Field of Classification Search ..................... 514/2
See application file for complete search history.

(56) References Cited

FOREIGN PATENT DOCUMENTS

JP            2004-155776 A    6/2004

OTHER PUBLICATIONS

Miyamoto, et al. Heparin-Binding EG-Like Growth Factor Is a Promising Target for Ovarian Cancer Therapy, Cancer Research 64(16):5720-5727 (2004).
Thogersen, et al., A Subclass of HER1 Ligands Are Prognostic Markers for Survival in Bladder Cancer Patients, Cancer Research 61(16):6227-6233 (2001).
Ongusaha, et al., HB-EGF Is a Potent Inducer of Tumor Growth and Angiogenesis, Cancer Research 64, 5283-5290 (2004).
Freeman, et al., Heparin-binding EGF Like Growth Factor Is an Autocrine Growth Factor for Human Urothelial Cells and Is Synthesized by Epithelial and Smooth Muscle Cells in the Human Bladder, Journal of Clinical Investigation,99(5):1028-1036 (1997).
Matsuda, et al., Multiple Mitogenic Pathways in Pancreatic Cancer Cells Are Blocked by a Truncated Epidermal Growth Factor Receptor, Cancer Research 62(19):5611-5617 (2002).
Kleeff, et al., The Cell-surface Heparan Sulfate Proteoglycan Glypican-1 Regulates Growth Factor Action in Pancreatic Carcinoma Cells and Is Overexpressed in Human Pancreatic Cancer, Journal of Clinical Investigation, 102(9):1662-1673 (1998).

Furuyama, et al., Role of E-cadherin in Peritoneal Dissemination of the Pancreatic Cancer Cell line, Panc-1, through regulation of cell to cell contact, Cancer Letters, 157(2):201-209 (2000).
Romano, et al., *Helicobacter pylori* Upregulates Expression of Epiderman Growth Factor-related Peptides, but InhibitsTheir Proliferative Effect in MKN 28 Gastric Mucosal Cells, The Journal of Clinical Investigation, 101(8):1604-1613 (1998).
Matsuoka, et al., Inhibition of invasion and lymph node metastasis of gastrointestinal cancer cells by R-94138, a matrix metalloproteinase inhibitor, Anticancer Research, 20:4331-4338 (2000).
Itoh el., IL-8 promotes cell proliferation and migration through metalloproteinase-cleavage proHB-EGF in human colon carcinoma cells, Cytokine, 29(6):275-282 (2005).
Wallasch et al., *Heliobacter pylori*-stimulated EGF receptor transactivation requires metalloprotease cleavage of HB-EGF, Biochemical and Biophysical Research Comm. 295(3):695-701 (2002).
Buzzi, et al., CRM 197 (nontoxic diptheria toxin):effects on advanced cancer patients, Cancer Immunol. Immunother, 53:1041-1048 (2004).
Silvio Buzzi, "Diptheria Toxin Treatment of Human Advanced Cancer", Cancer Research 42, 2054-2058, (May 1982).
Silvio Buzzi, et al.; "Phase I-II study of CRM197 administration to 50 advanced cancer patients", Clinical Cancer Research, vol. 5, #384 (Nov. 1999) (Supplement).
Silvio Buzzi, et al.; "CRM197: Phagocyte mediated antitumor activity followed by a connective proliferation tending to encapsule the tumor", Proceedings of the American Association for Cancer Research, vol. 43, #4529 (Mar. 2002).
Silvio Buzzi; "Diptheria Toxin in Cancer Therapy", The Lancet, 628-629 (Apr. 6, 1974).
Silvio Buzzi, et al.; Diptheria Toxoid immunotherapy of human advanced cancer, Proceedings of the American Association for Cancer Research, vol. 35, #3150 (Mar. 1994).
Silvio Buzzi, et al.; Immunological effects of a boiled diptheria toxoid on high risk cancer patients, Proceedings of the American Association for Cancer Research, vol. 38, #2662 (Mar. 1997).
Silvio Buzzi, et al.; "CRM197: effects in cancer patients", Proceedings of the American Association for Cancer Research, vol. 39, #2412 (Mar. 1998).
Silvio Buzzi, et al.; "Antitumor Effect of CRM197: Preferential Activity in Lymph Nodes", Proceedings of the American Association for Cancer Research, vol. 41, #1839 (Mar. 2000).
Silvio Buzzi, et al.; "Cancer Immunotherapy with CRM197, A Nontoxic Mutant of Diptheria Toxin", Abstracts of the Oncology—Molecular Medicine Congress, #185 (2001).

(Continued)

*Primary Examiner*—Christopher H Yaen
(74) *Attorney, Agent, or Firm*—Fitch, Even, Tabin & Flannery

(57) ABSTRACT

The present invention provides a cancer therapeutic agent containing as an active ingredient a substance, particularly CRM197 which inhibits the binding of HB-EGF to EGF receptor by binding to HB-EGF, wherein a cancer is selected from the group consisting of a bladder cancer, a colon cancer or peritoneal metastatic cancers of a stomach cancer and a pancreatic cancer.

7 Claims, 4 Drawing Sheets

OTHER PUBLICATIONS

Silvio Buzzi, et al.; "CRM197 antitumor activity: Possible mechanism of action", Proceedings of the American Association for Cancer Research, vol. 44, #3857 (Mar. 2003).

Silvio Buzzi, et al.; "CRM197: Effects of intravenous administration to advanced cancer patients", American Association for Cancer Research, #3803 (2004).

Silvio Buzzi, et al.; "CRM197 (nontoxic diptheria toxin): effects on advanced cancer patients", Cancer Immunol. Immunother 53, 1041-1048 (2004).

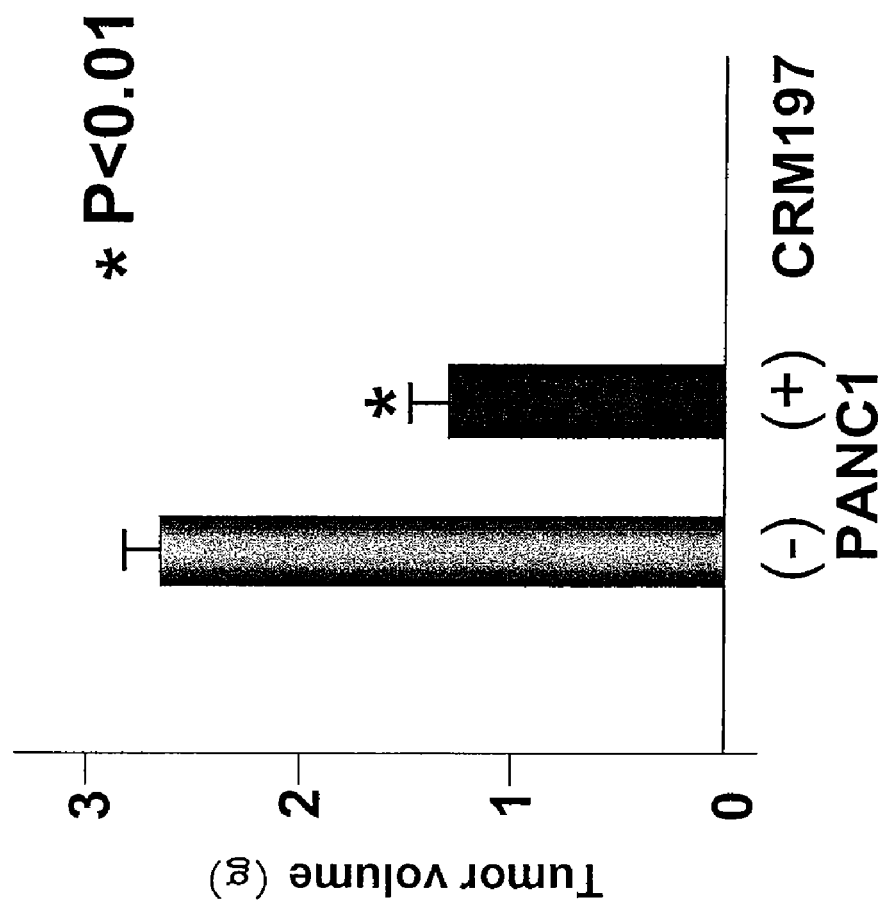

THERAPEUTIC AGENT FOR CANCER

This Application is a U.S. National Stage Application under 35 U.S.C. §371 of International Application PCT/JP2006/312321 filed Jun. 20, 2006, which designated the U.S. and was not published in English, and claims the foreign filing date benefits and priority Japanese Application 2005-181314 filed Jun. 21, 2005 and Japanese Application No. 2006-07581 filed Feb. 3, 2006 and the complete disclosure of each said application, including sequence listings, is incorporated herein by reference.

TECHNICAL FIELD

The present invention relates to a cancer therapeutic agent for a bladder cancer, a colon cancer, and peritoneal metastasis of a stomach cancer and a pancreatic cancer.

BACKGROUND ART

Diphtheria toxin or its mutant such as CRM197 has an activity to inhibit the binding of HB-EGF to EGF receptor by binding to an EGF-like domain in soluble and non-soluble (membrane-anchored) HB-EGF. A receptor binding domain in diphtheria toxin is involved in this binding.

Various studies have been performed on anti-cancer effects of CRM197. For example, it is described in Patent Document 1 that CRM197 is effective for a breast cancer, an ovarian cancer, a prostate cancer and a thyroid cancer. It is disclosed in Non-patent Literature 1 that when CRM197 was administered to patients with cancer having the metastasis, complete responses were observed in the breast cancer and a neuroblastoma, but the cancer progressed in cases of a non-small cell lung cancer, the colon cancer and the bladder cancer.

No effective anticancer agent is available for the peritoneal metastasis of the stomach cancer and the pancreatic cancer, whose prognosis is known to be poor. No effect of diphtheria toxin or its mutant such as CRM197 on these cancers have been known.

Patent Document 1: JP 2004-155776-A

Non-patent Literature 1: S. Buzzi, et al. Cancer Immunol. Immunother. (2004) 53: 1041-1048

DISCLOSURE OF INVENTION

Problem to be Solved by the Invention

It is an object of the present invention to provide an anti-cancer agent effective for a bladder cancer, a colon cancer, and peritoneal metastasis of a stomach cancer and a pancreatic cancer.

Means for Solving the Problem

As a result of an extensive study on anti-tumor effects of CRM197, the present inventor has found that CRM197 is effective for a bladder cancer, a colon cancer, or peritoneal metastasis of a stomach cancer and a pancreatic cancer.

The present invention relates to the following cancer therapeutic agents.

[1] A cancer therapeutic agent comprising as an active ingredient a substance which inhibits the binding of HB-EGF to EGF receptor by binding to HB-EGF, wherein the active ingredient is a mutant of diphtheria toxin which is a polypeptide having an activity to inhibit the binding of HB-EGF to EGF receptor and substantially having no toxicity of diphtheria toxin and wherein a cancer is selected from the group consisting of a colon cancer, a bladder cancer and a peritoneal metastatic cancer.

[2] The cancer therapeutic agent according to [1] which is a therapeutic agent for the bladder cancer.

[3] The cancer therapeutic agent according to [1] which is a therapeutic agent for the colon cancer.

[4] The cancer therapeutic agent according to [1] which is a therapeutic agent for the peritoneal metastatic cancer.

[5] The cancer therapeutic agent according to [4] wherein the peritoneal metastatic cancer is the cancer which has metastasized from the stomach cancer or the pancreatic cancer and has spread peritoneally.

[6] The cancer therapeutic agent according to any of [1] to [5] wherein the active ingredient is CRM197.

EFFECT OF THE INVENTION

According to the present invention, it is possible to effectively treat the bladder cancer, the colon cancer, and the peritoneal metastasis of the stomach cancer and the pancreatic cancer.

BRIEF DESCRIPTION OF DRAWINGS

FIG. 4 is a graph showing a peritoneal spread model. Human pancreatic cancer cell lines, PANC1 cells at $1 \times 10^7$ were intraperitoneally inoculated to nude mice, and CRM197 was intraperitoneally administered five times (50 mg/kg/week). On the 6th week after the inoculation, the entire peritoneal spread foci were removed, and their total weight was measured.

MODES FOR CARRYING OUT THE INVENTION

Figure 1:
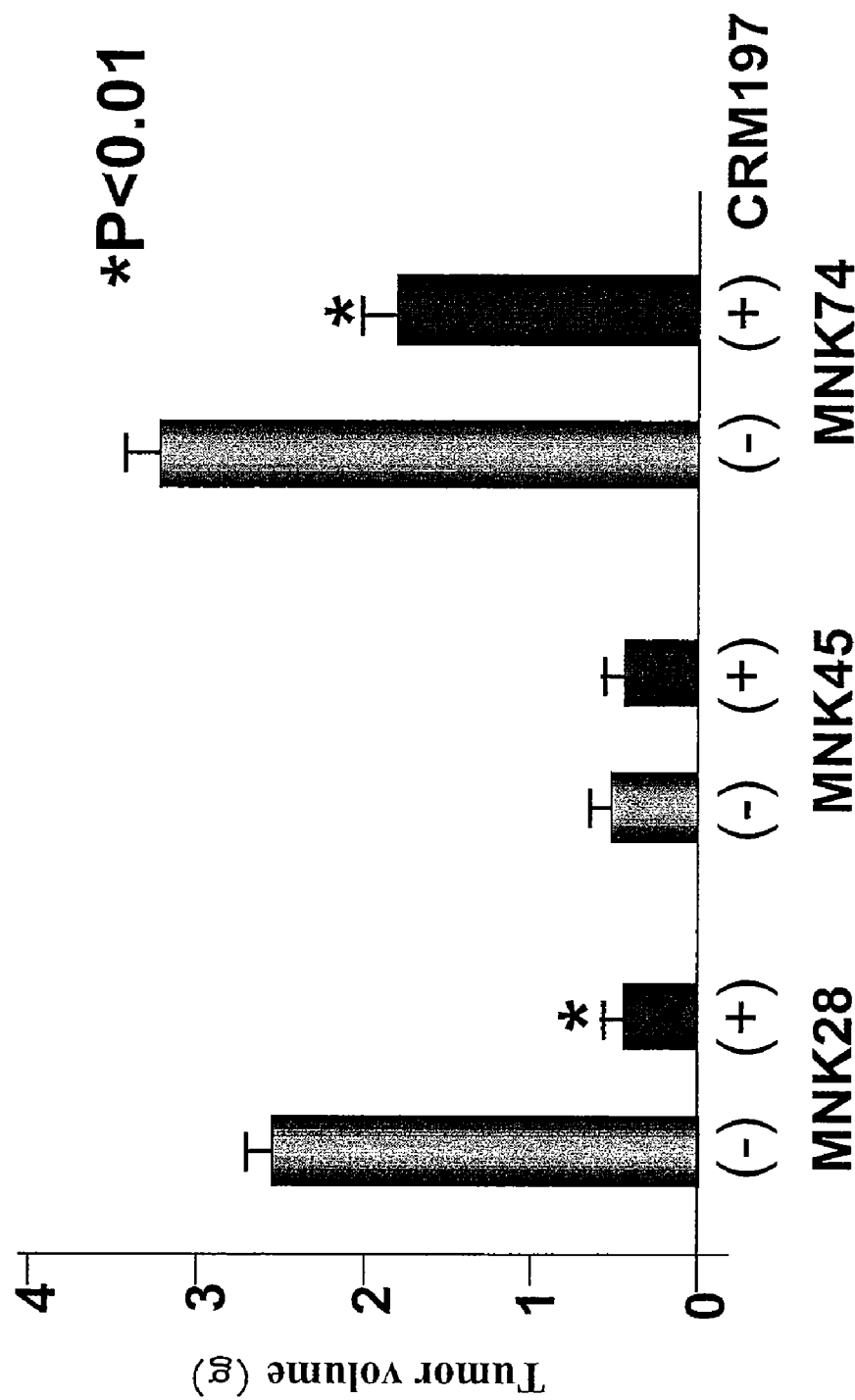
FIG. 1 is a graph showing a peritoneal spread model. Human stomach cancer cell lines, MKN28, MKN45 and MKN74 cells at $1 \times 10^7$ were intraperitoneally inoculated to nude mice, and CRM197 was intraperitoneally administered five times (50 mg/kg/week). On the 6th week after the inoculation, entire peritoneal spread foci were removed, and their total weight was measured.

The present invention relates to a therapeutic agent comprising as an active ingredient a substance which inhibits the binding of HB-EGF to EGF receptor by binding to HB-EGF, particularly a polypeptide which is diphtheria toxin mutant having an activity to inhibit the binding of HB-EGF to EGF receptor and substantially having no toxicity of diphtheria toxin, for treating at least one cancer selected from the group consisting of a colon cancer, a bladder cancer or peritoneal metastatic cancers of a stomach cancer and a pancreatic cancer.

The polypeptide comprising a receptor binding domain of diphtheria toxin is preferable as an example of the above substance. The particularly preferable above substance is either CRM197 or DT52E148K. For amino acid numbers in CRM197, the amino acid (Gly) at position 26 was numbered as No. 1 by removing a signal sequence (1 to 25) in an amino acid sequence in SEQ ID NO:1.

The receptor binding domain in diphtheria toxin can inhibit the binding of HB-EGF to EGF receptor by binding to HB-EGF. A polypeptide having one or more (e.g., several to several tens of) amino acid deletions, substitutions, insertions or additions in a catalytic action domain of diphtheria toxin to impair a part or all of the catalytic action is preferable as an example of the above polypeptide because of its low toxicity. The signal sequence of 25 amino acid residues may or may not be included.

In one preferable embodiment of the present invention, the above substance includes any of the following polypeptide (a), (b) or (c) having the activity to inhibit the binding of HB-EGF to EGF receptor:

(a) a polypeptide composed of parts of diphtheria toxin and containing at least the receptor binding domain of diphtheria toxin;

(b) a polypeptide composed of an amino acid sequence having one or more (e.g., several or several tens of) amino acid deletions, substitutions or additions in the receptor binding domain in the polypeptide (a); or (c) a complex polypeptide containing either the protein (a) or (b).

The receptor binding domain generally indicates a region from the position 378 to a C terminus (position 535), but it has been reported that a region of about 53 amino acid residues in a C terminal side has a receptor binding ability (J. Biol. Chem., 265:7331-7337, 1990).

Diphtheria toxin mutants such as CRM197 and DT52E148K are preferable as the active ingredient of the cancer therapeutic agent of the present invention because they have the low toxicity.

It is preferable in terms of eliminating side effects and enhancing safety that a toxic level in the substance of the present invention is equivalent to or less than that of CRM197. However, the present invention suggests that the toxicity contributes to the effect of a carcinostatic agent, and thus, it is also preferable in terms of enhancing the carcinostatic effect to have the toxicity at extremely low level equivalent to that of CRM197. Therefore, depending on a preparation formula, it is possible to appropriately select the toxic level of diphtheria toxin.

The toxic level of diphtheria toxin can be controlled by mutating the catalytic action domain essential for ADP ribosylation or deleting the parts or all of the catalytic action domain. In addition to this, those having a mutation in a transmembrane domain present between the catalytic action domain and the receptor binding domain become non-toxic or low toxic because the catalytic domain can not be internalized in cytoplasm. Therefore, it is likely to be able to also use diphtheria toxin having the mutation in this region as the carcinostatic agent.

The polypeptide containing the amino acid sequence from the position 378 to the position 535 corresponding to the receptor binding domain in the amino acid sequence of diphtheria toxin has the activity to inhibit the binding of HB-EGF to EGF receptor in the active ingredient of the present invention.

The preferable substance which is the active ingredient of the present invention includes (i) diphtheria toxin mutant keeping the receptor binding domain of diphtheria toxin and mutating (partial or total substitution, deletion insertion or addition) the catalytic action domain. Specific examples of such a mutant include CRM197, DT52E148K and GST-DT. These mutants substantially have no toxicity of diphtheria toxin and inhibit the binding of HB-EGF to EGF receptor. CRM 197 is the mutant having the mutation from Gly to Glu at position 52 when counted with the exception of the signal sequence of 25 amino acid residues; DT52E148K is the mutant having the mutation from Glu to Lys at position 148 in addition to the above mutation when counted with the exception of the signal sequence; and GST-DT is the protein containing the amino acid residues from positions 378 to 535 when counted with the exception of the signal sequence, which is bound to GST (glutathione S-transferase). The amino acid sequence (first 25 amino acid residues compose the signal sequence) of CRM197 is shown in SEQ ID NO:1, and a base sequence encoding it is shown in SEQ ID NO:2.

It has been already reported that CRM197 does not have the toxicity of diphtheria toxin, i.e., does not have an ADP ribosylation activity (T. Uchida and A. M. Pappenheimer Jr. (1972) Science 175, 901-903). It has been also known that the 148K mutant having the mutation at 148E has only the extremely weak activity (J. T. Barbieri and R. J. Collier (1987) Infect. Immun. 55, 1647-1651). DT52E148K which is a double mutant further having a 148K mutation in CRM197 which is a 52E mutant is preferable as the safer mutant.

A fragment containing the receptor binding domain can be prepared by synthesizing a DNA sequence of a receptor binding domain portion by PCR using a gene (Pβ197) encoding CRM197 incorporated in a plasmid as a template, inserting this in a multicloning site in an expression vector (pGEX-3X, pQE-30) for synthesizing a GST fusion protein or a histidine tag, incorporating the resulting plasmid in *Escherichia coli* and synthesizing the gene encoded by the plasmid in *Escherichia coli*.

The mutant having the mutation in the catalytic action domain can be made as follows. A CRM197 region is synthesized by PCR with the gene (Pβ197) encoding CRM197 incorporated in the plasmid as the template using as a primer a portion to be mutated. The primer is synthesized by introducing a point mutation so as to be mutated, and used. The mutant can be made by incorporating the synthesized DNA into a gene expression vector (pET-22b) for *Escherichia coli*, transforming *Escherichia coli* with the vector to express the mutant in *Escherichia coli*.

The therapeutic agent of the present invention is effective for the treatment of primary foci of the bladder cancer and the colon cancer, and metastatic foci (peritoneal metastasis) of the stomach cancer and the pancreatic cancer.

The therapeutic agent of the present invention is effective for the treatment of the cancer in which the expression of HB-EGF has been especially enhanced among growth factors in the EGF family.

The therapeutic agent of the present invention can be directly formulated from the above active ingredient, or can be formulated by combining the ingredient with a pharmaceutically acceptable carrier for pharmaceuticals.

The above therapeutic agent can be administered orally or parenterally (e.g., intravenous, intramuscular, intraperitoneal, subcutaneous or intradermal injection, or intrarectal administration, permucosal administration, administration via respiratory tract). When applied to peritoneally spread malignant tumors such as peritoneal metastasis of the stomach cancer and the pancreatic cancer, it is preferable in terms of being directly carried to the cancer cells to administer by intraperitoneal injection.

Formulations of the pharmaceutical composition orally administered can include but are to limited to, for example, tablets, granules, capsules, powders, liquids, suspensions and syrups, and the formulations of the pharmaceutical composition parenterally administered can include but are not limited to, for example, injectable agents, infusion agents, suppositories and percutaneous absorbers.

Types of additives for the preparation used for producing the therapeutic agent are not particularly limited and can be appropriately selected by those skilled in the art. For example, excipients, disintegrants or disintegrant aids, binders, lubricants, coating agents, bases, dissolving agents or dissolving agent aids, dispersants, suspending agents, emulsifiers, buffers, antioxidants, preservatives, tonicity agents, pH adjusters, dissolving agents and stabilizers can be used, and individual specific ingredients used for these purposes are well known to those skilled in the art.

As the additives for the preparation used for preparing the preparation for the oral administration, the excipient such as glucose, lactose, D-mannitol, starch or crystalline cellulose; the disintegrant or the disintegrant aid such as carboxymethylcellulose, starch or calcium carboxymethylcellulose; the binder such as hydroxypropylcellulose, hydroxypropylmethylcellulose, polyvinyl pyrrolidone or gelatin; the lubricant such as magnesium stearate or talc; coating agent such as hydroxypropylmethylcellulose, sucrose, polyethylene glycol or titanium oxide; and the base such as petrolatum, liquid paraffin, polyethylene glycol, gelatin, kaolin, glycerine, purified water and hard fat can be used.

As the additives for the preparation which can be used for preparing the preparation for the injection or the infusion, the dissolving agent or the dissolving aid such as distilled water for the injection, saline and propylene glycol which can constitute an aqueous injectable agent or an injectable agent dissolved in use; the tonicity agent such as glucose, sodium chloride, D-mannitol and glycerine; and the pH adjuster such as inorganic acids, organic acid, inorganic bases or organic bases can be used.

Although an amount of the active ingredient contained in the therapeutic agent of the present invention varies depending on a dosage form or an administration route of the therapeutic agent and can not be defined rigidly, it can be typically determined by appropriately selecting from the range of about 0.0001% to 70% in the final preparation.

The therapeutic agent of the present invention can be administered to mammalian animals including human beings, particularly the human beings.

The amount of the therapeutic agent of the present invention to be administered should be appropriately increased or decreased depending on the condition e.g., an age, gender, body weight and symptoms of the patient, and the administration route, and is preferably in the range of about 1 μg to 50 mg per 1 kg of the body weight as the amount of the active ingredient per day per adult. The pharmaceutical in the above amount to be administered may be administered once daily or administered by dividing into several times. The pharmaceutical may be administered once weekly over 6 to 8 weeks, or administered every other day over 2 to 3 weeks, or administered daily for 10 to 14 days.

As the carcinostatic agent capable of being combined with the cancer therapeutic agent of the present application, taxol, taxotere, 5-FU, cisplatin, carboplatin, adriamycin and camptothecin and the like are exemplified.

EXAMPLES

The present invention will be described below in detail based on Examples, but it goes without saying that the present invention is not limited to these Examples.

Example 1

A peritoneal spread model. Human stomach cancer cell lines, MKN28, MKN45 and MKN74 cells at $1 \times 10^7$ were intraperitoneally inoculated to nude mice, and CRM197 was intraperitoneally administered five times (50 mg/kg/week). On the 6th week after the inoculation, the entire peritoneal spread foci were removed, and their total weight was measured (FIG. 1).

Example 2

Figure 2:
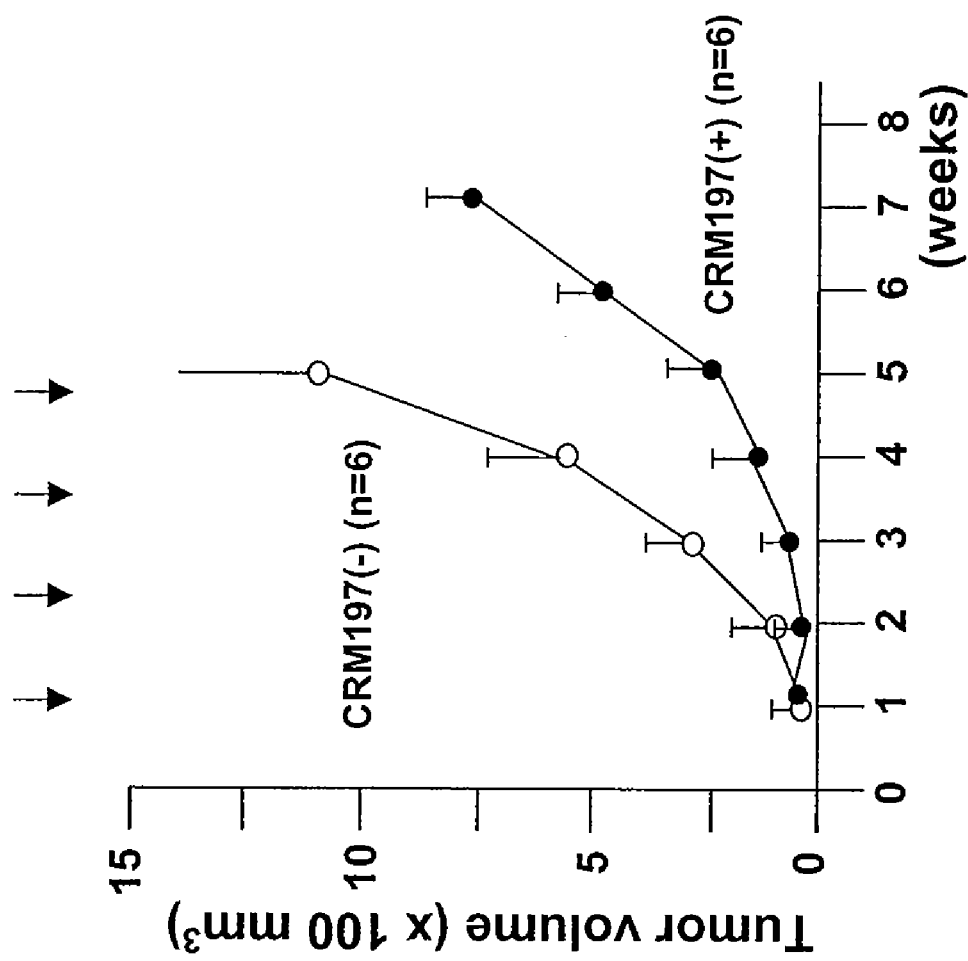
FIG. 2 is a graph showing the effect of CRM197. Human bladder cancer cell line, KK47 cells ($5 \times 10^6$ cells) were inoculated to the back of nude mice by injecting subcutaneously. For the nude mice in one group, CRM197 in an amount of 50 mg/kg/week was intraperitoneally administered (arrows) from the 7th day after inoculating the cells. The nude mice to which no CRM197 had been administered were used as controls.

A tumorigenicity experiment using nude mice was performed. Human bladder cancer cell line, KK47 cells cultured in RPMI+10% FBS were washed with EDTA/PBS(−), and collected using 0.25% trypsin. The cells were washed twice with RPMI+10% FBS and twice with RPMI (serum free), and the cells at $5 \times 10^6$ were added to 250 μL of RPMI (containing the serum). This was inoculated to the back of nude mice by injecting subcutaneously. In one group of the nude mice, CRM197 in an amount of 50 mg/kg/week was administered intraperitoneally from the 7th day after inoculating the cells. CRM197 was administered once a week over 3 weeks. The nude mice to which no CRM197 had been administered were used as the control. A relationship of an administration time and a tumor volume is shown in FIG. 2. The tumor volume was obtained by measuring a major axis and a minor axis of the produced tumor weekly and calculating from (Major axis)×(Minor axis)×(Minor axis)×½.

Example 3

Figure 3:
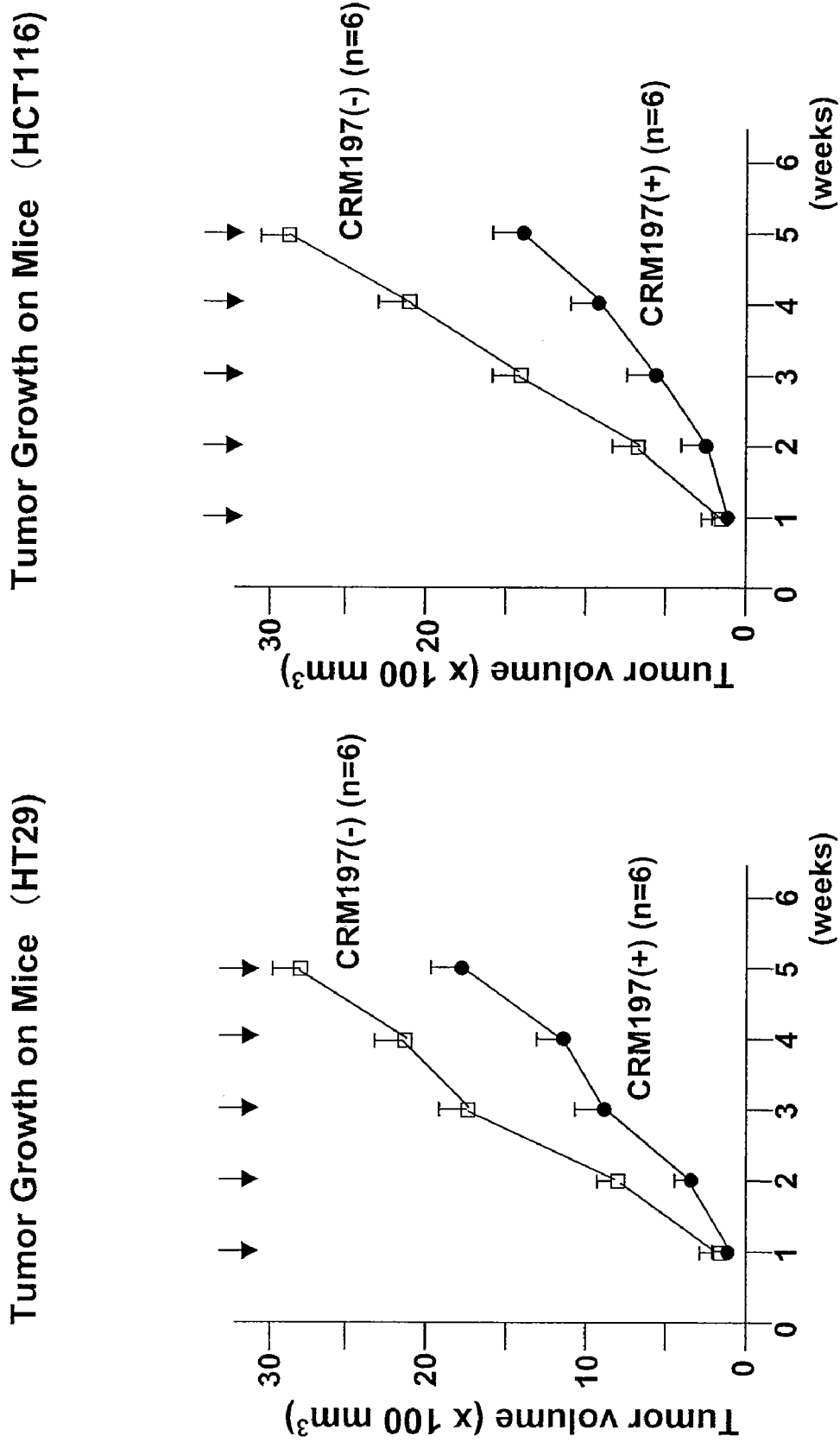
FIG. 3. Human colon cancer cell line, HT29 cells or HCT116 cells ($5 \times 10^6$ cells) were inoculated to the back of nude mice by injecting subcutaneously. For the nude mice in one group, CRM197 in an amount of 50 mg/kg/week was intraperitoneally administered (arrows) from the 7th day after inoculating the cells. The nude mice to which no CRM197 had been administered were used as controls.

A tumorigenicity experiment using nude mice was performed. Human colon cancer cell line, HT29 or HCT116 cells (available from American Type Culture Collection [ATCC]) cultured in RPMI+10% FBS were washed with EDTA/PBS (−), and collected using 0.25% trypsin. The cells were washed twice with RPMI+10% FBS and twice with RPMI (serum free), and the cells at $5 \times 10^6$ were added to 250 μL of RPMI (containing the serum). This was inoculated to the back of nude mice by injecting subcutaneously. In one group of the nude mice, CRM197 in an amount of 50 mg/kg/week was administered intraperitoneally from the 7th day after inoculating the cells. CRM197 was administered once a week over 3 weeks. The nude mice to which no CRM197 had been administered were used as the control. The relationship of the administration time and the tumor volume is shown in FIG. 3. The tumor volume was obtained by measuring the major axis and the minor axis of the produced tumor weekly and calculating from (Major axis)×(Minor axis)×(Minor axis)×½.

Example 4

A peritoneal spread model. Human pancreatic cancer cell line, PANC1 cells at $1 \times 10^7$ were intraperitoneally inoculated to nude mice, and CRM197 was intraperitoneally administered five times (50 mg/kg/week). On the 6th week after the inoculation, the entire peritoneal spread foci were removed, and their total weight was measured (FIG. 4).

From results in these Examples, it has been found that the administration of CRM197 inhibited the tumor growth in all cases.

The invention claimed is:

1. A method for treating peritoneal metastatic cancer in a patient in need of such treatment, comprising administering to said patient a tumor-inhibiting amount of a cancer therapeutic agent including CRM197 as an active ingredient.

2. A method for treating a cancer selected from the group consisting of colon cancer, bladder cancer, and peritoneal metastatic cancer in a patient in need of such treatment, wherein the expression of HB-EGF has been especially enhanced in said cancer, said method comprising administering to said patient a tumor-inhibiting amount of a cancer therapeutic agent including CRM197 as an active ingredient.

3. The method of claim 2, wherein the therapeutic agent is for the treatment of colon cancer.

4. The method of claim 2, wherein the therapeutic agent is for the treatment of bladder cancer.

5. The method of claim 2, wherein the therapeutic agent is for the treatment of peritoneal metastatic cancer.

6. The method of claim 2, wherein an amount of the active ingredient in the therapeutic agent is selected from about 0.0001% to about 70%.

7. The method of claim 1, wherein the dosage is about 1 µg to about 50 µg per about 1 kg of weight.

* * * * *

UNITED STATES PATENT AND TRADEMARK OFFICE
CERTIFICATE OF CORRECTION

PATENT NO.        : 7,700,546 B2
APPLICATION NO.   : 11/917706
DATED             : April 20, 2010
INVENTOR(S)       : Eisuke Mekada and Shingo Miyamoto It is certified that error appears in the above-identified patent and that said Letters Patent is hereby corrected as shown below:

On the Title Page

Item (73) Assignee: Delete "The Research foundation for Microbial Diseases of Osaka c/o Osaka" and Insert --THE RESEARCH FOUNDATION FOR MICROBIAL DISEASES OF OSAKA UNIVERSITY--

Signed and Sealed this
Twenty-first Day of October, 2014

Michelle K. Lee
*Deputy Director of the United States Patent and Trademark Office*

SEQUENCE LISTING

<160> NUMBER OF SEQ ID NOS: 2

<210> SEQ ID NO 1
<211> LENGTH: 560
<212> TYPE: PRT
<213> ORGANISM: Artificial Sequence
<220> FEATURE:
<223> OTHER INFORMATION: Description of Artificial Sequence: Synthetic
      CRM197 polypeptide sequence

<400> SEQUENCE: 1

```
Met Ser Arg Lys Leu Phe Ala Ser Ile Leu Ile Gly Ala Leu Leu Gly
1               5                   10                  15

Ile Gly Ala Pro Pro Ser Ala His Ala Gly Ala Asp Asp Val Val Asp
            20                  25                  30

Ser Ser Lys Ser Phe Val Met Glu Asn Phe Ser Ser Tyr His Gly Thr
        35                  40                  45

Lys Pro Gly Tyr Val Asp Ser Ile Gln Lys Gly Ile Gln Lys Pro Lys
    50                  55                  60

Ser Gly Thr Gln Gly Asn Tyr Asp Asp Asp Trp Lys Glu Phe Tyr Ser
65                  70                  75                  80

Thr Asp Asn Lys Tyr Asp Ala Ala Gly Tyr Ser Val Asp Asn Glu Asn
                85                  90                  95

Pro Leu Ser Gly Lys Ala Gly Gly Val Val Lys Val Thr Tyr Pro Gly
            100                 105                 110

Leu Thr Lys Val Leu Ala Leu Lys Val Asp Asn Ala Glu Thr Ile Lys
        115                 120                 125

Lys Glu Leu Gly Leu Ser Leu Thr Glu Pro Leu Met Glu Gln Val Gly
    130                 135                 140

Thr Glu Glu Phe Ile Lys Arg Phe Gly Asp Gly Ala Ser Arg Val Val
145                 150                 155                 160

Leu Ser Leu Pro Phe Ala Glu Gly Ser Ser Ser Val Glu Tyr Ile Asn
                165                 170                 175

Asn Trp Glu Gln Ala Lys Ala Leu Ser Val Glu Leu Glu Ile Asn Phe
            180                 185                 190

Glu Thr Arg Gly Lys Arg Gly Gln Asp Ala Met Tyr Glu Tyr Met Ala
        195                 200                 205

Gln Ala Cys Ala Gly Asn Arg Val Arg Arg Ser Val Gly Ser Ser Leu
    210                 215                 220

Ser Cys Ile Asn Leu Asp Trp Asp Val Ile Arg Asp Lys Thr Lys Thr
225                 230                 235                 240

Lys Ile Glu Ser Leu Lys Glu His Gly Pro Ile Lys Asn Lys Met Ser
                245                 250                 255

Glu Ser Pro Asn Lys Thr Val Ser Glu Glu Lys Ala Lys Gln Tyr Leu
            260                 265                 270

Glu Glu Phe His Gln Thr Ala Leu Glu His Pro Glu Leu Ser Glu Leu
        275                 280                 285

Lys Thr Val Thr Gly Thr Asn Pro Val Phe Ala Gly Ala Asn Tyr Ala
    290                 295                 300

Ala Trp Ala Val Asn Val Ala Gln Val Ile Asp Ser Glu Thr Ala Asp
305                 310                 315                 320

Asn Leu Glu Lys Thr Thr Ala Ala Leu Ser Ile Leu Pro Gly Ile Gly
                325                 330                 335

Ser Val Met Gly Ile Ala Asp Gly Ala Val His His Asn Thr Glu Glu
```

```
                    340              345              350
Ile Val Ala Gln Ser Ile Ala Leu Ser Ser Leu Met Val Ala Gln Ala
            355              360              365
Ile Pro Leu Val Gly Glu Leu Val Asp Ile Gly Phe Ala Ala Tyr Asn
    370              375              380
Phe Val Glu Ser Ile Ile Asn Leu Phe Gln Val Val His Asn Ser Tyr
385              390              395              400
Asn Arg Pro Ala Tyr Ser Pro Gly His Lys Thr Gln Pro Phe Leu His
                405              410              415
Asp Gly Tyr Ala Val Ser Trp Asn Thr Val Glu Asp Ser Ile Ile Arg
            420              425              430
Thr Gly Phe Gln Gly Glu Ser Gly His Asp Ile Lys Ile Thr Ala Glu
        435              440              445
Asn Thr Pro Leu Pro Ile Ala Gly Val Leu Leu Pro Thr Ile Pro Gly
    450              455              460
Lys Leu Asp Val Asn Lys Ser Lys Thr His Ile Ser Val Asn Gly Arg
465              470              475              480
Lys Ile Arg Met Arg Cys Arg Ala Ile Asp Gly Asp Val Thr Phe Cys
                485              490              495
Arg Pro Lys Ser Pro Val Tyr Val Gly Asn Gly Val His Ala Asn Leu
            500              505              510
His Val Ala Phe His Arg Ser Ser Glu Lys Ile His Ser Asn Glu
        515              520              525
Ile Ser Ser Asp Ser Ile Gly Val Leu Gly Tyr Gln Lys Thr Val Asp
    530              535              540
His Thr Lys Val Asn Ser Lys Leu Ser Leu Phe Phe Glu Ile Lys Ser
545              550              555              560

<210> SEQ ID NO 2
<211> LENGTH: 1683
<212> TYPE: DNA
<213> ORGANISM: Artificial Sequence
<220> FEATURE:
<223> OTHER INFORMATION: Description of Artificial Sequence: Synthetic
      CRM197 polynucleotide sequence

<400> SEQUENCE: 2
gtgagcagaa aactgtttgc gtcaatctta atagggggcgc tactggggat aggggcccca      60
ccttcagccc atgcaggcgc tgatgatgtt gttgattctt ctaaatcttt tgtgatggaa     120
aacttttctt cgtaccacgg gactaaacct ggttatgtag attccattca aaaaggtata     180
caaaagccaa atctggtac acaaggaaat tatgacgatg attggaaaga gttttatagt     240
accgacaata aatacgacgc tgcgggatac tctgtagata tgaaaacccc gctctctgga     300
aaagctggag gcgtggtcaa agtgacgtat ccaggactga cgaaggttct cgcactaaaa     360
gtggataatg ccgaaactat taagaaagag ttaggtttaa gtctcactga accgttgatg     420
gagcaagtcg gaacggaaga gtttatcaaa aggttcggtg atggtgcttc gcgtgtagtg     480
ctcagccttc ccttcgctga ggggagttct agcgttgaat atattaataa ctgggaacag     540
gcgaaagcgt taagcgtaga acttgagatt aattttgaaa cccgtggaaa acgtggccaa     600
gatgcgatgt atgagtatat ggctcaagcc tgtgcaggaa atcgtgtcag gcgatcagta     660
ggtagctcat tgtcatgcat aaatcttgat tgggatgtca taagggataa aactaagaca     720
aagatagagt ctttgaaaga gcatggccct atcaaaaata aaatgagcga aagtcccaat     780
aaaacagtat ctgaggaaaa agctaaacaa tacctagaag aatttcatca acggcatta     840
```

```
gagcatcctg aattgtcaga acttaaaacc gttactggga ccaatcctgt attcgctggg      900
gctaactatg cggcgtgggc agtaaacgtt gcgcaagtta tcgatagcga aacagctgat      960
aatttggaaa agacaactgc tgctctttcg atacttcctg gtatcggtag cgtaatgggc     1020
attgcagacg gtgccgttca ccacaataca gaagagatag tggcacaatc aatagcttta     1080
tcgtctttaa tggttgctca agctattcca ttggtaggag agctagttga tattggtttc     1140
gctgcatata attttgtaga gagtattatc aatttatttc aagtagttca taattcgtat     1200
aatcgtcccg cgtattctcc ggggcataaa acgcaaccat ttcttcatga cgggtatgct     1260
gtcagttgga acactgttga agattcgata atccgaactg gttttcaagg ggagagtggg     1320
cacgacataa aaattactgc tgaaaatacc ccgcttccaa tcgcgggtgt cctactaccg     1380
actattcctg gaaagctgga cgttaataag tccaagactc atatttccgt aaatggtcgg     1440
aaaataagga tgcgttgcag agctatagac ggtgatgtaa cttttttgtcg ccctaaatct     1500
cctgtttatg ttggtaatgg tgtgcatgcg aatcttcacg tggcatttca cagaagcagc     1560
tcggagaaaa ttcattctaa tgaaatttcg tcggattcca taggcgttct tgggtaccag     1620
aaaacagtag atcacaccaa ggttaattct aagctatcgc tattttttga aatcaaaagc     1680
tga                                                                    1683
```